United States Patent [19]

Nelson et al.

[11] Patent Number: 4,540,365

[45] Date of Patent: Sep. 10, 1985

[54] DENTAL CLEANSING SYSTEM

[75] Inventors: Edwin A. Nelson, York; Ronald C. Webb, Red Lion, both of Pa.

[73] Assignee: Advanced Design Corporation, Dallastown, Pa.

[21] Appl. No.: 554,612

[22] Filed: Nov. 23, 1983

[51] Int. Cl.[4] ............................................. A61C 3/02
[52] U.S. Cl. ..................................... 433/88; 433/125
[58] Field of Search .................. 433/88; 51/427, 438, 51/439, 12

[56] References Cited

U.S. PATENT DOCUMENTS

| 794,122 | 7/1905 | Rosengarten . | |
|---|---|---|---|
| 2,071,472 | 2/1937 | Pletcher . | |
| 2,290,979 | 7/1942 | Luce . | |
| 2,324,250 | 7/1943 | Voerge . | |
| 2,325,517 | 7/1943 | Howard . | |
| 2,376,287 | 5/1945 | Sorrentino . | |
| 2,376,616 | 5/1945 | Oechsle et al. . | |
| 2,405,854 | 8/1946 | Ruemelin . | |
| 2,696,049 | 12/1954 | Black . | |
| 2,742,738 | 4/1956 | Hall . | |
| 2,825,135 | 3/1958 | Tilden . | |
| 3,525,154 | 8/1970 | Lieb . | |
| 3,769,753 | 11/1973 | Fleischer . | |
| 3,775,849 | 12/1973 | Condon . | |
| 3,863,628 | 2/1975 | Vit . | |
| 3,882,638 | 5/1975 | Black ........................................ | 51/12 |
| 3,972,123 | 8/1976 | Black . | |
| 4,174,571 | 11/1979 | Gallant . | |
| 4,249,899 | 2/1981 | Davis ..................................... | 433/80 |
| 4,462,803 | 7/1984 | Landgraf .............................. | 433/88 |

*Primary Examiner*—Robert Peshock
*Attorney, Agent, or Firm*—Finnegan, Henderson, Farabow, Garrett & Dunner

[57] ABSTRACT

A hand-held dental cleansing system for delivery of an abrasive laden stream against a tooth which is to be cleaned. The system is adapted to be coupled to sources of pressurized liquid and gas, and includes handpiece having a canister containing the abrasive material. Through various valves on the handpiece controlling the liquid and gas streams, the abrasive material is transported from the canister to a mixing chamber within a nozzle on the handpiece. The liquid or gas streams may be combined with the abrasive laden stream within the mixing chamber so as to result in a homogenous stream delivered to a single point on the tooth being cleaned. The canister, mixing chamber and connecting conduit may be constructed as a single unit adapted for easy removal and replacement by a fresh unit.

20 Claims, 11 Drawing Figures

4,540,365

DENTAL CLEANSING SYSTEM

BACKGROUND OF THE INVENTION

The present invention relates to the field of dental cleansing equipment and, more particularly, to a system for delivering an abrasive laden stream for use in cleaning teeth.

The surfaces of teeth are subject to deposits of foreign materials, broadly classified as stain and calculus. The source of such foreign material ranges from natural fluids, such as blood and saliva, to food, drink and tobacco smoke. Regardless of the source, however, stain and calculus usually result in discoloration of the tooth surface.

It is well-known that stain and calculus may be removed from a tooth by an abrasive action. Prior art methods for providing such action include the use of abrasive pastes containing pumice or silex, as well as the use of air-abrasive equipment. In the latter case, a stream of abrasive laden gas is directed against the tooth which is to be cleaned and the repetitive action of abrasive particles striking the tooth surface produces the desired cleaning.

Air abrasive equipment exmplifying such prior art devices are described and claimed in U.S. Pat. Nos. 3,882,638 and 3,972,123 to Robert B. Black. Another system is the subject of U.S. Pat. No. 4,174,571 to Ben J. Gallant. The apparatus and methods disclosed in these patents provide for the delivery of an abrasive laden gaseous stream surrounded by a plurality of discrete streams of liquid. The liquid streams are employed to enclose the abrasive material during delivery and prevent its premature disperal before the surface of the tooth is encountered.

In each of these prior art devices, the abrasive material is kept in containers in a supply cabinet and delivered to the tooth via a handpiece connected to said cabinet. The cabinet also houses the control mechanisms, e.g. valves, pumps, etc., which create the abrasive laden stream delivered to the handpiece. Since supplies of pressurized air and liquid are already available in many other pieces of dental equipment, the need for an additional cabinet to house the abrasive and control circuitry is an undesirable use of critical office and operating space.

Furthermore, in such systems the abrasive must be removed and all abrasive-carrying lines cleaned each night so as to prevent clogging of the system during subsequent use. This is a time-consuming procedure and can be very dirty. Such problems detract from the attractiveness of purchasing and using air-abrasive equipment.

SUMMARY OF THE INVENTION

Accordingly, it is an object of the invention to provide a dental cleansing system completely contained within a handpiece, including a supply of abrasive material, which is compact and easy to use.

It is another object of the present invention to facilitate ease of maintenance of a dental cleansing system through the use of replacable canisters of abrasive material.

It is a further object of the present invention to permit removal and replacement of all abrasive-carrying passages simultaneously with replacement of an abrasive canister, thereby contributing further to ease of maintenance.

Additional objects and advantages of the present invention will be set forth in part in the description that follows and in part will be obvious from the description or may be learned by practice of the invention. The objects and advantages of the invention may be realized and obtained by the methods and apparatus particularly pointed out in the appended claims.

To achieve the objects and in accordance with the purpose of the invention, as embodied and as broadly described herein, a hand-held system adapted to be connected to gas and liquid supply means for delivering an abrasive to a tooth to be cleaned, comprises: first means connected to the gas supply means for producing a controlled gas stream; second means connected to the liquid supply means for producing a controlled liquid stream; a canister containing an abrasive material, the canister having an inlet for receiving one of the gas and liquid streams and an outlet for permitting exiting of an abrasive laden stream; and a mixing chamber receiving the gas, liquid and abrasive laden streams for combining and directing the streams so as to strike a common point on the tooth being cleaned.

According to a further embodiment of the invention, a hand-held system adapted to be connected to gas and liquid supply means for delivering an abrasive to a tooth to be cleaned, comprises: first means connected to the gas supply means for producing a controlled gas stream; second means connected to the liquid supply means for producing a controlled liquid stream; a canister containing an abrasive material and having an outlet to permit exiting of an abrasive laden stream; manually actuatable means coupled to the canister for producing the abrasive laden stream; and a mixing chamber receiving the gas, liquid and abrasive laden streams for combining and directing the streams so as to strike a common point on the tooth being cleaned.

The accompanying drawings, which are incorporated in and constitute a part of this specification, illustrate several embodiments of the invention and, together with the description, serve to explain the principles of the invention.

DESCRIPTION OF THE PREFERRED EMBODIMENTS

Figure 1:
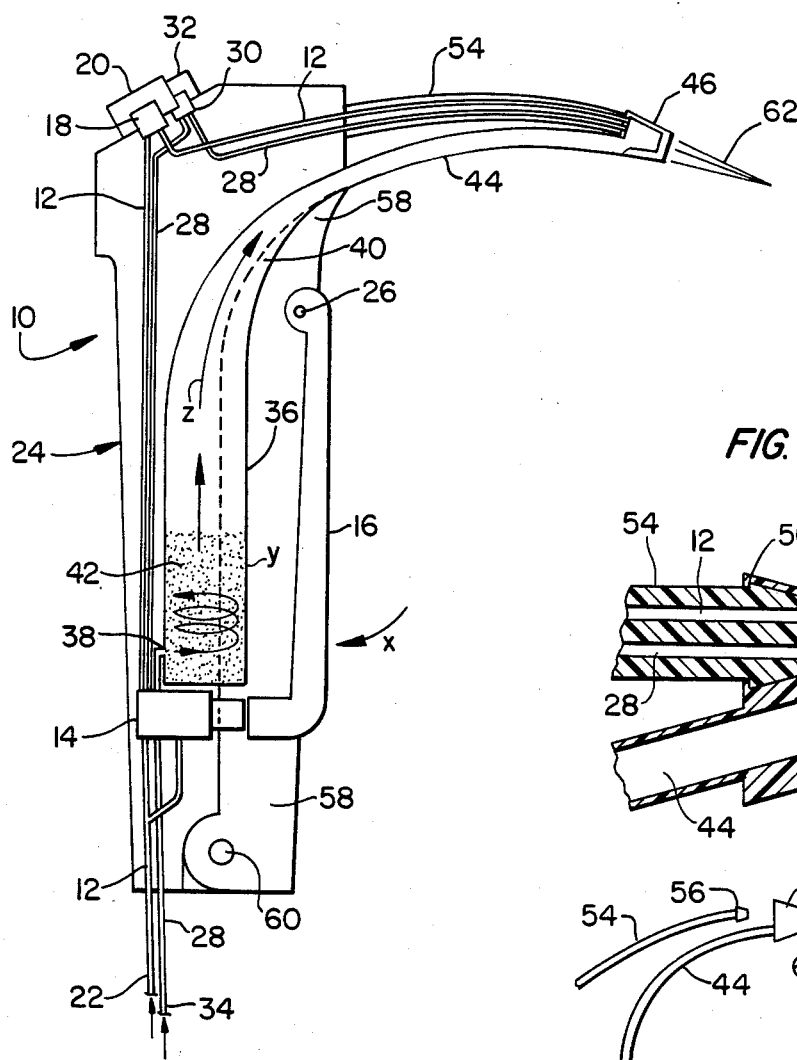
FIG. 1 is a cross-sectional view of a preferred embodiment of a dental cleansing system in accordance with the present invention.

Reference will now be made in detail to the presently preferred embodiments of the invention, examples of which are illustrated in the accompanying drawings. Throughout the drawings, like reference characters are used to indicate like elements.

A preferred embodiment of a dental cleansing system according to the present invention is shown in cross-sectional view in FIG. 1 and is generally designated by reference character 10. As explained further hereinbelow, the system 10 is connected to liquid and gas supply means (not shown) which provide pressurized liquid and gas, respectively. Such supply means are well known in the art and are found in many pieces of dental equipment, making them convenient for use with the present system. Typically, the liquid and gas comprise water and air, respectively, although other liquids and other gases may be used without departing from the spirit or scope of the present invention.

According to the present invention, first means are provided connected to the gas supply means for producing a controlled gas stream. As embodied herein, the first means comprise conduit 12, valve 14 with lever 16, and valve 18 with pushbutton 20. Conduit 12 comprises tubing, such as rubber, plastic or the like, and is connected at one end 22 to the gas supply means. Valves 14 and 18 are manually actuatable valves in communication with conduit 12 so as to control the delivery of the gas stream. Such valves are well-known in the art and need not be described for purposes of the present invention.

The foregoing elements, as well as those described hereinbelow, are provided within or located on a handpiece 24. Valve 14, located within the handpiece, is actuated by means of lever 16 hinged on the outer surface of handpiece 24 via a pin 26. When lever 16 is depressed, valve 14 allows the gas stream to pass therethrough. Valve 18 is actuatable via a pushbutton 20, or by other actuation mechanisms, exposed at the head of handpiece 24. Depressing pushbutton 20 causes a gas stream to pass from the gas supply means through valve 18. Valves 14 and 18 are actuatable independently of each other.

According to the present invention, second means are provided connected to the liquid supply means for producing a controlled liquid stream. As embodied herein, the second means include conduit 28, valve 30 and pushbutton 32. Conduit 28 consists of tubing, such as plastic, rubber or the like, and is coupled at one end 34 to the liquid supply means (not shown). Valve 30 and pushbutton 32, of a type and arrangement similar to that of valve 18 and pushbutton 20 described above, can be manually actuated to permit a stream of liquid to pass therethrough.

The present invention further provides a canister containing an abrasive material, said canister having an inlet for receiving one of the gas and liquid streams, and an outlet permitting exiting of an abrasive laden stream. As embodied herein, the canister is designated by reference character 36, and has an inlet 38 and an outlet 40. Cansister 36 contains an abrasive material 42.

Canister 36 is preferably constructed as a plastic cylinder, although other materials and other shapes may be employed. Inlet 38 is formed in the wall of canister 36 to receive the gas stream emitted by conduit 12 upon actuation of valve 14 via lever 16. Introduction of the gas stream into canister 36 causes turbulence of abrasive material 42, forcing the material to exit via outlet 40 as an abrasive laden stream. Outlet 40 may be an opening in the wall of canister 36 or may comprise a narrowed end of canister 36, as shown in FIG. 1. The outlet of canister 36 is connected to a conduit 44.

Figure 2:
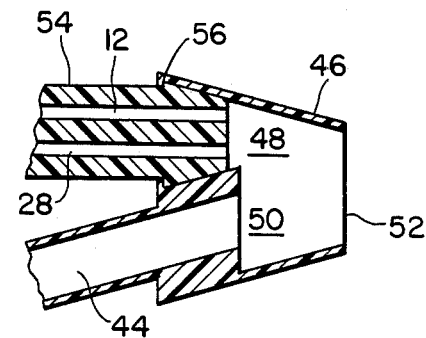
FIG. 2 is a cross-sectional view showing details of the mixing chamber of the cleansing system of FIG. 1.

The present invention also provides a mixing chamber receiving the gas, liquid and abrasive laden streams for combining and directing the streams so as to strike a common point on the tooth being cleaned. As embodied herein, the mixing chamber is designated by reference character 46. As best shown in FIG. 2, mixing chamber 46 is a frusto-conical nozzle having first inlet means 48 adapted to receive the gas stream via conduit 12 and the liquid stream via conduit 28. Second inlet means 50 receives the abrasive laden stream from coonduit 44. Within mixing chamber 46, all of the streams are combined as the result of turbulence created when each stream hits the interior wall of the chamber, causing a single homogenous stream to exit the chamber at outlet 52. Accordingly, the output stream contacts a single point on the surface of the tooth being cleaned (not shown), regardless of the specific combination of gas, liquid or abrasive which make up the output stream.

The interchangeability of the canister and/or mixing chamber will now be described with reference to FIGS. 1, 2 and 3. Handpiece 24, which contains canister 36, has an extending neck 54 in which are disposed conduits 12 and 28. Extending generally parallel to neck 54 from handpiece 22 is conduit 44 which carries the abrasive laden stream. According to the preferred embodiment illustrated in FIG. 2, neck 54 is snap-fit into the first inlet means 48 of mixing chamber 46 by means of an engaging lip arrangement 56. Conduit 44, on the other hand, is integrally formed with mixing chamber 46 and not separable therefrom. Thus, neck 54 may be unsnapped from mixing chamber 46 by exerting sufficient pressure to overcome the engagement of lip 56, whereupon mixing chamber 46, conduit 44 and canister 36 may be removed as a single unit. A new unit of similar construction may then be put in place of the old unit.

To facilitate access to and removal of canister 36 relative handpiece 24, the handpiece may be provided with a hatch 58 hinged via a pin 60. By swiveling hatch 58 about pin 60, the inside of handpiece 24 is exposed which permits removal and replacement of canister 36. Hatch 58 may be maintained in a closed position on handpiece 24 via a snap arrangement (not shown), or a hinge spring (not shown) positioned about pin 60, or by other means known in the art. Further, hatch 58 may conveniently carry lever 16 and pin 26 which are in contact with valve 14 via an opening in the hatch.

Figure 3A:
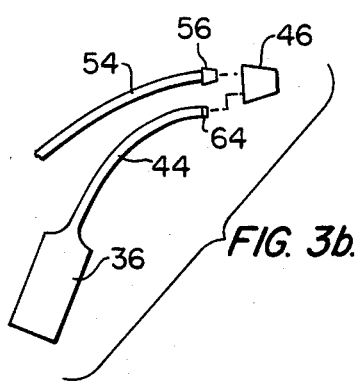
FIGS. 3a, 3b and 3c are perspective views illustrating three embodiments of a removable canister and mixing means of the cleansing system of FIG. 1.
Figures 3B, 3C:
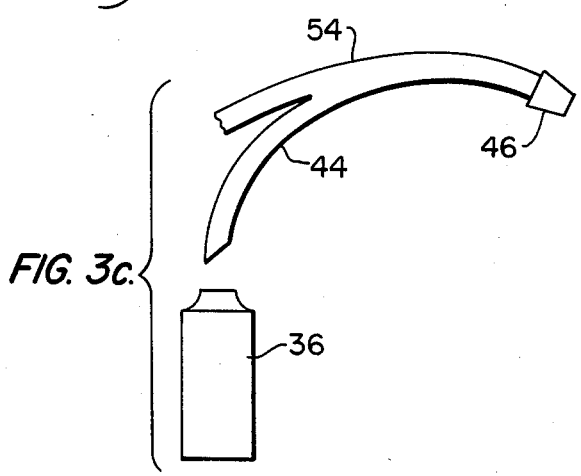

Alternative arrangements of removable canister 36 and related parts are illustrated in FIGS. 3a, 3b and 3c. FIG. 3a illustrates the above-described arrangement in which canister 36, conduit 44 and mixing chamber 46 are formed as a single unit removable upon disengagement of neck 54 along lip 56. As also shown in this figure, a plug 62 may be provided to cover the outlet end 52 (FIG. 2) of mixing chamber 46 to keep out foreign matter and prevent contamination of the system between uses, if desired. Moreover, plug 62 may be provided as part of each replaceable unit (i.e., canister, conduit and mixing chamber) so as to prevent contamination of the unit during shipping and storage; plug 62 would thus be removed immediately prior to usage. Plug 62 may be snap-fitted into mixing chamber 46 via an engaging lip arrangement of the same type as is designated by reference character 56.

According to the embodiment illustrated in FIG. 3b, mixing chamber 46 may further be separated from conduit 44, whereby container 36 and conduit 44 may be removed as a single unit. For this purpose, the tip of conduit 44 may be provided with a lip arrangement 64 to provide a snap-fit with a corresponding lip provided in the second inlet means 50 (FIG. 2) of mixing chamber 46.

In the embodiment shown in FIG. 3c, mixing chamber 46 is formed integrally with conduit 44 and neck 54, such that only container 36 is removable. In this case, a snap-fit arrangement may be employed for providing sealing engagement between container 36 and conduit 44. Alternately, the tip of conduit 44 may be sharpened so as to pierce the outlet end of container 36, provided a snug fit may still be obtained. Sealing arrangements of this type are known in the art and need not be described for purposes of understanding the present invention.

Operation of the device will now be explained with reference to the preferred embodiment illustrated in FIG. 1. To prepare the system for operation, conduits 12 and 28 are coupled, respectively, to sources of pressurized gas and liquid. In addition, hatch 58 of handpiece 24 is opened so that a fresh canister 36 containing abrasive material 42 can be placed therein. The canister is fit into handpiece 24 such that conduit 12 extends through inlet 38 to provide communication between the gas stream carried therein and the interior of canister 36. This communication can be provided, for example, by means of a sharpened tip on conduit 12 which punctures the wall of canister 36 as it is placed into handpiece 12. Outlet end 40 of canister 36, in communication with conduit 44 with mixing chamber 46 formed integrally therewith is then aligned generally parallel to neck 54 so that the tip of the neck can be fitted into and communicate with inlet 48 (FIG. 2) of the mixing chamber. Hatch 58 may then be closed by pivoting on hinge pin 60, whereby lever 16 is realigned so as to operate valve 14.

To facilitate convenient use of the system, handpiece 24 is shaped so that the body of the handpiece fits comfortably in the palm of the hand, with the operator's fingers resting against lever 16. In this position, the operator's thumb can be used to actuate either one or both of pushbuttons 20 and 32, the pushbuttons preferably being positioned sufficiently close to each other so that they can be actuated simultaneously, if so desired. Holding the handpiece in the aforementioned manner, the operator directs extending neck 54 and conduit 44 so as to point the forthcoming stream against the area of the tooth which is to be cleaned.

Figure 4A:
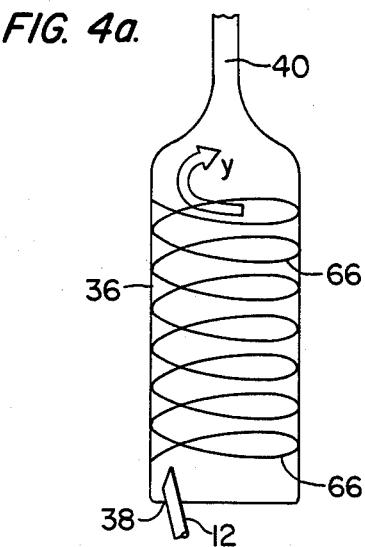
FIGS. 4a and 4b are diagrams illustrating the mixing operation which occurs within the canister of the cleansing system of FIG. 1.
Figure 4B:
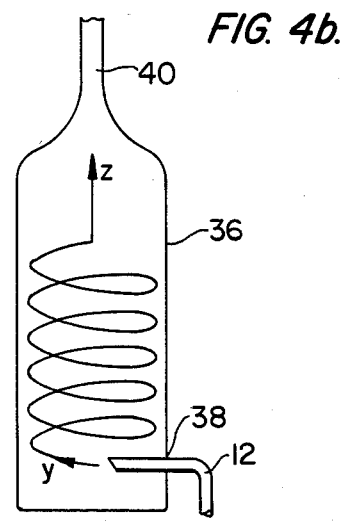

The specific composition of stream 58 can be controlled by means of lever 16 and pushbuttons 20 and 32. In the first instance, depressing lever 16 in the direction indicated by the arrow x causes valve 14 to open and the gas stream to enter canister 36. The gas stream entering at inlet 38 creates turbulence within abrasive material 42 to produce a swirling action, as indicated by arrow y. As the abrasive material is swirled, it travels upwards within canister 36, in the direction shown by arrow z, ultimately exiting the canister at outlet 40. The resulting abrasive laden stream travels through conduit 44 and into mixing chamber 46, from which it exits in stream 62 to strike the tooth being cleaned. FIGS. 4a and 4b illustrate the manner in which the swirling action is created within canister 36. In the embodiment shown in FIG. 4a, conduit 12 and inlet 38 are at the bottom of canister 36, while the interior walls of canister 36 are provided with a series of screw-threads or grooves 66. As the gas stream exits conduit 12, the resulting turbulence involving abrasive material 42 (not shown) is translated into a spiral motion due to the interference of grooves 66. This produces the spiral motion indicated by arrow z.

In an alternative embodiment illustrated in FIG. 4b, conduit 12 and inlet 38 are disposed in the sidewall of canister 36 so that the incoming gas stream is already directed at an angle to produce the spiral motion y. At the outlet end 40 of canister 36, narrowing of the canister produces the second motion, indicated by arrow z.

Referring again to FIG. 1, it may be desirable to add a gas stream to the abrasive laden stream so at to increase the velocity at which the abrasive particles impact the tooth being cleaned. This can be accomplished by depressing pushbutton 20 simultaneously with lever 16. Pressure on pushbutton 20 causes valve 18 to open and the gas stream to travel along conduit 12, through neck 54, into mixing chamber 46. Within the mixing chamber, the gas stream is combined with the abrasive laden stream so as to exit outlet 52 (FIG. 2) as a unitary stream 62. As stated above, the addition within the mixing chamber of the gas stream to the abrasive laden stream increases the velocity, and hence the effect, of the abrasive particles in the cleaning process.

By means of pushbutton 32, it is also possible to add liquid to the output stream 62, thereby preventing unwanted dispersion of the abrasive particles within the patient's mouth, while also providing a liquid medium for easy removal of the abrasive. The addition of the liquid stream is accomplished by depressing pushbutton 32 to open valve 30. The liquid under pressure thus travels along conduit 28 through neck 54 and into mixing chamber 46 via first inlet 48 (FIG. 2). Within the mixing chamber, the liquid is combined with the gas stream and abrasive laden stream, and exits at outlet 52 as part of the homogenous stream 62.

It should be appreciated from the foregoing that any one of the streams may be generated separately, independent from generation of the other streams, or in any combination with the other streams. For example, if only a liquid stream is desired, e.g., to wet a portion of the patient's mouth, this can be accomplished by depressing pushbutton 32, alone. Likewise, a stream of gas can be dispensed alone, such as to dry a portion of the patient's tooth, by depressing only pushbutton 26. Accordingly, the dental cleansing system of the present invention finds use in applications beyond merely air-abrasive operations, and can function as an overall useful tool in the dentist's office.

Several modifications of the system described above have been envisioned and are considered within the scope and spirit of the present invention. For example, abrasive material 42 disposed in canister 36 may consist of either a dry powder, comprising abrasive particles, or may consist of abrasive particles suspended within a fluid, such as a cream. In either case, introducing the gas stream into the canister via inlet 38 will result in an abrasive laden stream being delivered from outlet 40 through conduit 44 to mixing chamber 46. Sufficient velocity to produce the desired cleaning action can be imparted by supplementing the abrasive laden stream in mixing chamber 46 with the gas stream produced in response to actuation of valve 18. Abrasives suitable for such applications include calcium carbonate or sodium biocarbonate, whereas a cream suitable for fluid suspension could be toothpaste, fluoride or the like, thereby giving a polishing effect at the same time.

A further modification of the system illustrated in FIG. 1 can be achieved by switching the connections to the liquid and gas supply means, i.e., coupling conduit 12 to the liquid supply means and conduit 28 to the gas supply means. Correspondingly, pushbutton 32 will serve to introduce a gas stream into mixing chamber 46, whereas pushbutton 20 will serve to introduce a liquid stream into the chamber. Actuation of lever 16 will open valve 14 to inject the liquid stream through inlet 38 into canister 36. As long as sufficient pressure is available in the liquid stream, it can interact with abrasive material 42 to produce the identical turbulence and swirling motion described above. Accordingly, a liquid-based abrasive laden stream is delivered through outlet 40 into conduit 44 and mixing chamber 46, so that the cleansing system can still accomplish the desired cleaning operation.

In the case of the modification described above, it should be appreciated that the abrasive material 42 is preferably not soluble in the liquid introduced via conduit 12, so as to avoid undesirable clogging of the system. If water is used as the liquid, the abrasive material may comprise a microencapsulated powder subsequently broken down and dissolved by enzymes within the month. Soluble abrasives may be used, however, provided that the solubility is such as to avoid clogging prior to full utilization of the abrasive material within the canister. In the event clogging does occur, canister 36 together with conduit 44 and mixing chamber 46 can be removed and replaced with a fresh, unclogged unit.

Further embodiments of a dental cleansing system according to the present invention will now be discussed with respect to FIGS. 5-8. Since each of these embodiments differs from the preferred embodiment only with respect to details of the replaceable canister 36 and related actuating means, most of the structural details discussed above are not illustrated in FIGS. 5 through 8 for sake of simplicity. it is to be understood, however, that such structures are, in fact, incorporated in and form a part of the alternative embodiments discussed below. The discussion below, however, focuses only on those elements which differ from the structures presented in the preferred embodiment illustrated in FIG. 1.

Figure 5:
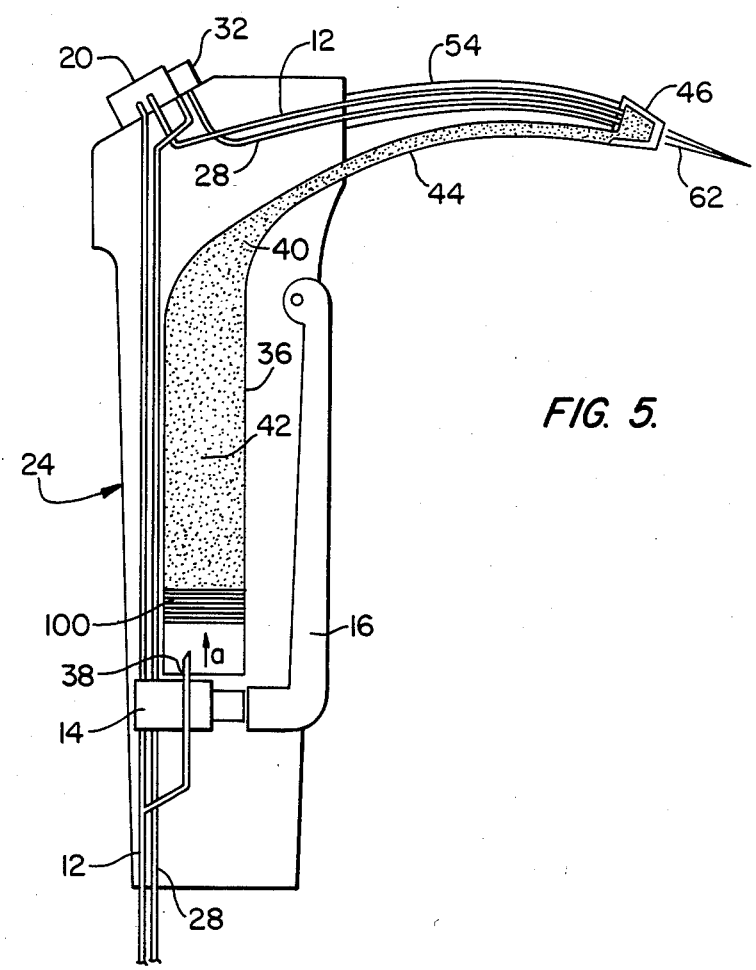
FIG. 5 is a cross-sectional view of a dental cleansing system in accordance with a second embodiment of the present invention.

Turning to the second embodiment of a dental cleansing system according to the present invention illustrated in FIG. 5, it is seen that canister 36 is provided with a plunger 100 disposed in the interior portion thereof. Plunger 100 is arranged so that a stream of gas or liquid entering the lower portion of the canister via inlet 38 causes upward movement of the plunger in the direction indicated by the arrow a. The plunger acts as a piston to drive abrasive 42, whether in powder form or suspended in a fluid, upwards through outlet 40 and conduit 44 into mixing chamber 46. Additional gas and/or liquid streams can be mixed with the abrasive stream in chamber 46 by means of either one or both of pushbuttons 20 and 32 in the manner described hereinabove.

Figure 6:
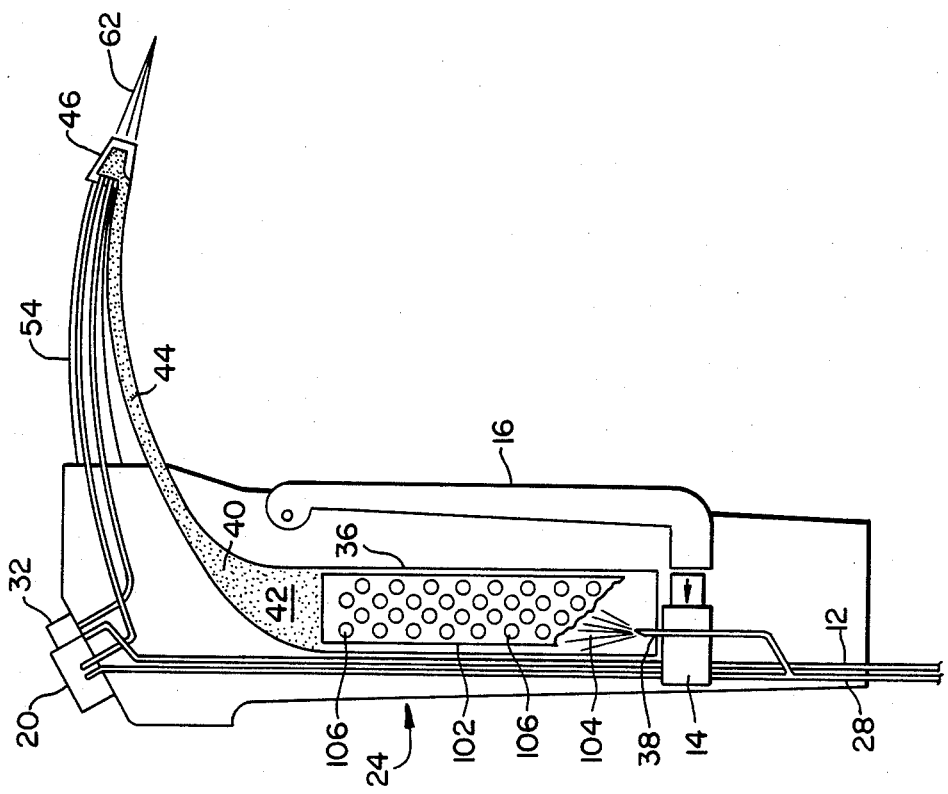
FIG. 6 is a cross-sectional view of a dental cleansing system in accordance with a third embodiment of the present invention.

A third embodiment of a dental cleansing system according to the present invention is illustrated in FIG. 6. According to this embodiment, abrasive material 42 is disposed within container 36 in a compressed form, such as a cartridge 102. Thus, as a liquid stream 104 is introduced into canister 36, the liquid stream 104 dissolves the abrasive cartridge 102 and frees the individual abrasive particles. The dissolved abrasive material carried in fluid 104 exits outlet 40 as an abrasive laden stream. In the manner described above with respect to the other embodiments, this abrasive laden stream is carried on to mixing chamber 46 where it may be combined, as desired, with the liquid or gas streams. Once all of cartridge 102 has been dissolved, canister 36 together with conduit 44 and mixing chamber 46 may be removed and replaced as described above. To aid in dissolving the cartridge, a plurality of holes 106 may be provided therein so that liquid stream 104 freely circulates through the cartridge.

Figure 7:
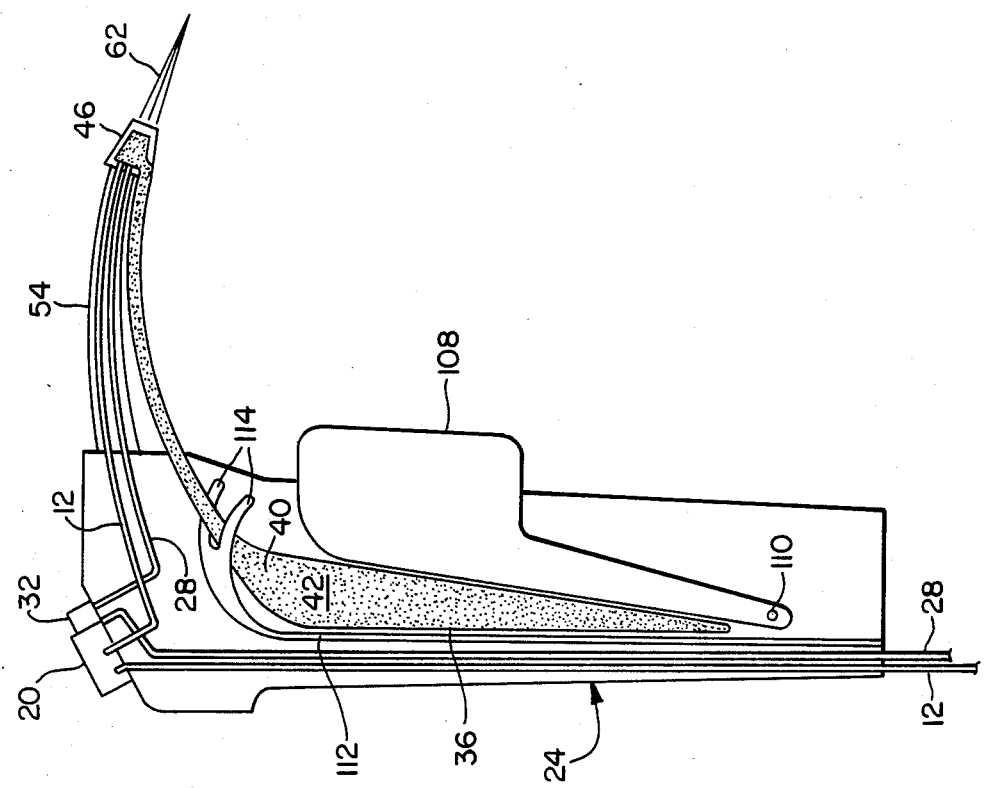
FIG. 7 is a cross-sectional view of a dental cleansing system in accordance with a fourth embodiment of the present invention.
Figure 8:
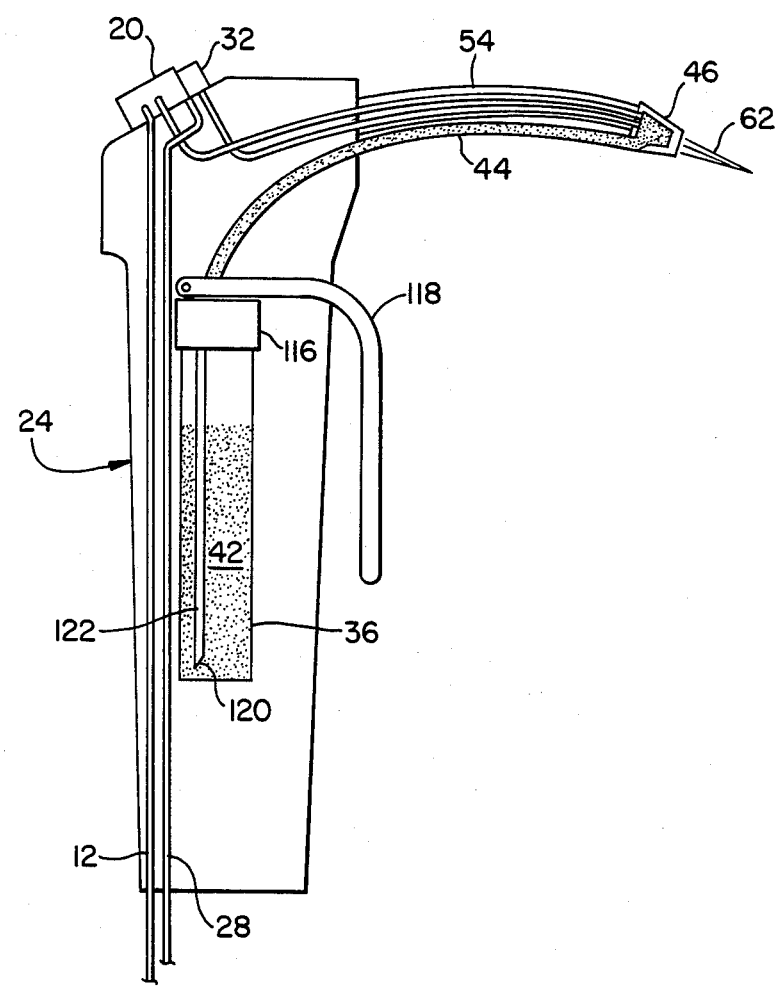
FIG. 8 is a cross-sectional view of a dental cleansing system in accordance with a fifth embodiment of the present invention.

In the embodiments of the present invention illustrated in FIGS. 7 and 8, abrasive material 42 is delivered from canister 36 via manually actuatable means, i.e., without use of either the liquid or gas streams. Referring to the fourth embodiment shown in FIG. 7, canister 36 comprises a compressible bladder or bag, such as is made of pliable plastic, which contains abrasive material 42 suspended in a cream or other fluid. Canister 36 is compressed by manual pressure exerted on a trigger 108 which is hinged on handpiece 24 via a pin 110. To provide a backstop for exerting pressure via trigger 108, a rigid arm 112 is fixedly secured within handpiece 24. The upper end 114 of arm 112 is forked to ensure that canister 36 remains in axial alignment with the arm. Pressure on trigger 108 causes the abrasive laden cream 42 to move upwards as a stream into mixing chamber 46. The abrasive laden stream delivered to the mixing chamber can then be mixed with either one or both of the liquid and gas streams from conduits 12 and 28, respectively, for dispensing in the manner described above.

A further embodiment of the present invention is illustrated in FIG. 8, in which abrasive material 42 suspended in a fluid within canister 36 is dispensed via a manually operable pump 116. That is, manual pressure on hinged pump lever 118 causes pump 116 to draw the material into the open end 120 of a pickup tube 122 in communication with conduit 44. The abrasive laden stream carried through conduit 44 to mixing chamber 46 may then be combined and dispensed to the tooth, in the manner already described above.

Mechanisms suitable for use as pump 116 are well known in the art and need not be described for purposes of the present invention. Pump 116 can be affixed to the interior of handpiece 24 so that action on pump lever 118 does not disturb the positioning of either the pump or of canister 36. When the abrasive material has been depleted, canister 36 may be separated from pump 116 by, for example, corresponding screw threads on the top of canister 36 and the inside of pump 116. Other sealing arrangements may be provided such as the snap-fit lip 56 illustrated in FIG. 2 in connection with mixing chamber 46, so as to permit easy removal and replacement of canister 36.

The present invention may therefore be summarized as providing a dental cleansing system in a compact hand-held unit from which a canister of abrasive material easily may be replaced. By manipulating the various triggers and pushbuttons disposed on the handpiece of the system, different compositions of material can be delivered in a stream from the nozzle of the handpiece and directed against the tooth being cleaned. Regardless of the composition of the stream, all of its components are combined within the mixing chamber of the nozzle to produce a homogenous stream which contacts a single point on the tooth.

The canister can be removed and replaced in a variety of ways. These range from removal of the canister, alone, to removal of the canister and attached conduit, to removal of the canister, conduit and mixing chamber. In the latter case, the three components can be formed integrally with one another and replaced as a single unit. The canister can be used as a single dosage unit, with a new canister being inserted for each patient. This will assure that the highest sanitary conditions will be maintained.

Furthermore, in view of the various methods of delivery of the abrasive material, the abrasive can be provided within the canister as either a dry powder or as abrasive particles suspended in a fluid, such as a cream.

It will be apparent to those skilled in the art that modifications and variations can be made in the dental cleansing system of the present invention. The invention in its broader aspects is, therefore, not limited to the specific details, representative methods and apparatus, and illustrative examples shown and described herein. For example, the described system may find use in jewelry cleaning, in dental laboratories, and other applications in which abrasive cleaning is appropriate. Thus, it is intended that all matter contained in the foregoing description are shown in the accompanying drawings shall be interpreted as illustrative and not in a limiting sense.

What is claimed is:

1. A hand-held system adapted to be connected to gas and liquid supply means for delivering an abrasive to a tooth to be cleaned, comprising:
   first means connected to the gas supply means for producing a controlled gas stream;
   second means connected to the liquid supply means for producing a controlled liquid stream;
   a canister containing an abrasive material, said canister having an inlet for receiving one of said gas and liquid streams, and an outlet permitting exiting of an abrasive laden stream;
   a mixing chamber receiving said gas, liquid and abrasive laden streams for combining and directing said streams so as to strike a common point on the tooth being cleaned; and
   a unitary handpiece for containing said first and second means, said canister and said mixing chamber, said handpiece having means for removably mounting said canister to permit replacement by another canister.

2. A system as recited in claim 1 wherein said first means includes first and second manually actuatable valves, said gas stream being connected to said inlet of said canister via said first valve and to said mixing chamber via said second valve.

3. The system as recited in claim 2 wherein said canister includes a piston driven by said gas stream for compressing said abrasive laden stream to said mixing chamber.

4. The system as recited in claim 2 wherein said first and second valves are independently actuatable to selectively deliver said gas stream and said abrasive laden stream to said mixing chamber.

5. The system as recited in claim 1 wherein said second means includes third and fourth manually actuatable valves, said liquid stream being connected to said inlet of said canister via said third valve and to said mixing chamber via said fourth valve.

6. The system as recited in claim 5 wherein said canister includes a piston driven by said liquid stream for compressing said abrasive material and delivering said abrasive laden stream to said mixing chamber.

7. The system as recited in claim 5 wherein said third and fourth valves are independently actuatable to selectively deliver said liquid stream and said abrasive laden stream to said mixing chamber.

8. The system as recited in claim 5 wherein said abrasive material comprises a solid block of particle abrasives which dissolves upon contact with said liquid stream.

9. The system as recited in claim 1 wherein said abrasive material comprises a dry powder.

10. The system as recited in claim 1 wherein said abrasive material comprises abrasive particles suspended in a fluid.

11. The system as recited in claim 1 wherein said mixing chamber comprises a frustoconical nozzle having first inlet means for receiving said liquid and gas streams, and second inlet means for receiving said abrasive laden stream.

12. The system as recited in claim 11 wherein said first and second means are conveniently separable from said first inlet means, and said canister together with said mixing means are conveniently removable from said handpiece to permit replacement by another canister and mixing means.

13. A hand-held system adapted to be connected to gas and liquid supply means for delivering an abrasive to a tooth to be cleaned, comprising:
   first means connected to the gas supply means or producing a controlled gas stream;
   second means connected to the liquid supply means for producing a controlled liquid stream;
   a canister containing an abrasive material and having an outlet to permit exiting of an abrasive laden stream;
   manually actuatable means coupled to said canister for producing said abrasive laden stream;
   a mixing chamber receiving said gas, liquid and abrasive laden streams for combining and directing said streams so as to strike a common point on the tooth being cleaned; and
   a unitary handpiece for containing said first and second means, said canister, said manually actuatable means and said mixing chamber, said handpiece having means for removably mounting said canister to permit replacement by another canister.

14. The system as recited in claim 13 wherein said first means includes a first manually actuatable valve for controlling delivery of said gas stream to said mixing chamber, and said second means includes a second manually actuatable valve for controlling delivery of said liquid stream to said mixing chamber.

15. The system as recited in claim 14 wherein said first and second valves are operable independently of each other and independently of said manually actuatable means.

16. The system as recited in claim 13 wherein said abrasive material comprises abrasive particles suspended in a fluid.

17. The system as recited in claim 16 wherein said manually actuatable means comprises a pump.

18. The system as recited in claim 16 wherein said container comprises a compressible bladder and said manually actuatable means comprises lever means for exerting a force to collapse said bladder.

19. The system as recited in claim 13 wherein said mixing chamber comprises a frustoconical nozzle having first inlet means for receiving said liquid and gas streams, and second inlet means for receiving said abrasive laden stream.

20. The system as recited in claim 19 wherein said first and second means are conveniently separable from said first inlet means, and said canister together with said mixing means are conveniently removable to permit replacement by another canister and mixing chamber.

* * * * *